US011172886B2

United States Patent
Wernow et al.

(10) Patent No.: US 11,172,886 B2
(45) Date of Patent: *Nov. 16, 2021

(54) HYDRATION SYSTEM AND METHOD THEREOF

(71) Applicant: Xennial IP LLC, Canton, OH (US)

(72) Inventors: Kathryn A. Wernow, Canton, OH (US); Howard L. Wernow, Canton, OH (US)

(73) Assignee: Xennial IP LLC, Canton, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/851,904

(22) Filed: Apr. 17, 2020

(65) Prior Publication Data

US 2020/0265939 A1 Aug. 20, 2020

Related U.S. Application Data

(63) Continuation of application No. 15/691,144, filed on Aug. 30, 2017, now Pat. No. 10,664,571, which is a (Continued)

(51) Int. Cl.
*G09B 19/00* (2006.01)
*A61B 5/00* (2006.01)
(Continued)

(52) U.S. Cl.
CPC .......... *A61B 5/6887* (2013.01); *A61B 5/4875* (2013.01); *G09B 19/00* (2013.01);
(Continued)

(58) Field of Classification Search
CPC ............. G06F 19/3418; G06F 19/3481; A61B 5/6887; A61B 5/4875; A61B 5/6895;
(Continued)

(56) References Cited

U.S. PATENT DOCUMENTS 8,903,671 B2 12/2014 Park et al.
8,909,543 B2 12/2014 Tropper et al.
(Continued)

OTHER PUBLICATIONS http://www.hydracoach.com/applications/index.html, 4 pages. Sportline Intelligent Water Bottle by HydraCoach, Inc. Document is undated but was printed from the pertinent website on Mar. 13, 2015.
(Continued)

*Primary Examiner* — Michael C Grant
(74) *Attorney, Agent, or Firm* — Sand, Sebolt & Wernow Co., LPA; Howard L. Wernow

(57) ABSTRACT

A communicative water bottle includes communication logic and wireless transmission logic technology electronically connected with a variety of sensors either on the water bottle or located remote from the water bottle. The sensors on the bottle create digital data associated with amount of fluid in the bottle and change thereof. The sensors remote from the bottle, which can be on an activity tracker, create digital data associated with an activity being performed by a user, such as running, or the absence of activity, such as remaining sedentary. A display on the bottle can indicate to the user the amount of fluid consumed or a reminder that fluid should be consumed. The fluid consumption data syncs with other remote devices such as mobile applications executable on smartphones.

2 Claims, 3 Drawing Sheets

Related U.S. Application Data continuation of application No. 14/657,300, filed on Mar. 13, 2015, now Pat. No. 9,792,409.

(51) Int. Cl.
*G16H 20/30* (2018.01)
*G16H 40/67* (2018.01)
*G16H 20/13* (2018.01)
*A61B 5/11* (2006.01)

(52) U.S. Cl.
CPC ............. *G16H 20/13* (2018.01); *G16H 20/30* (2018.01); *G16H 40/67* (2018.01); *A61B 5/1118* (2013.01); *A61B 5/6895* (2013.01); *A61B 5/7455* (2013.01); *A61B 2503/10* (2013.01); *A61B 2562/0219* (2013.01)

(58) Field of Classification Search
CPC .......... A61B 2562/0219; A61B 5/1118; A61B 2503/10; A61B 5/7455
USPC ........................................................ 434/247
See application file for complete search history.

(56) References Cited

U.S. PATENT DOCUMENTS

| | | | |
|---|---|---|---|
| 8,935,119 B2 | 1/2015 | Yuen | |
| 8,938,368 B2 | 1/2015 | Yuen et al. | |
| 8,941,500 B1* | 1/2015 | Faaborg | H04W 68/00 340/573.1 |
| 8,942,953 B2 | 1/2015 | Yuen et al. | |
| 2008/0058900 A1* | 3/2008 | Berthelsdorf | G16H 40/67 607/59 |
| 2014/0278139 A1* | 9/2014 | Hong | A61B 5/1118 702/19 |
| 2014/0303790 A1* | 10/2014 | Huang | G16H 20/60 700/281 |
| 2014/0340221 A1 | 11/2014 | Yuen et al. | |
| 2014/0343443 A1 | 11/2014 | Yuen et al. | |
| 2014/0343892 A1 | 11/2014 | Yuen et al. | |
| 2014/0358012 A1 | 12/2014 | Richards et al. | |
| 2014/0372045 A1* | 12/2014 | Keski-Pukkila | A61B 5/6887 702/19 |
| 2014/0375428 A1 | 12/2014 | Park | |
| 2014/0375452 A1 | 12/2014 | Yuen et al. | |
| 2014/0377729 A1 | 12/2014 | Yuen et al. | |
| 2014/0379275 A1 | 12/2014 | Yuen et al. | |
| 2015/0018991 A1 | 1/2015 | Arnold et al. | |
| 2015/0025393 A1 | 1/2015 | Hong et al. | |
| 2015/0025394 A1 | 1/2015 | Hong et al. | |
| 2015/0108026 A1* | 4/2015 | Azimi | G16H 20/60 206/459.1 |
| 2015/0122688 A1 | 5/2015 | Dias et al. | |
| 2015/0182797 A1* | 7/2015 | Wernow | A61B 5/6887 434/247 |
| 2016/0022209 A1* | 1/2016 | Fraisl | A61B 5/7282 600/590 |
| 2016/0051191 A1* | 2/2016 | Miller | A61B 5/681 600/300 |
| 2016/0143583 A1* | 5/2016 | Jeukendrup | A45F 3/16 600/301 |
| 2016/0220184 A1* | 8/2016 | Manion | G01F 13/008 |
| 2016/0235374 A1* | 8/2016 | Miller | A61B 5/0537 |
| 2017/0017776 A1* | 1/2017 | Soulos | G16H 20/30 |

OTHER PUBLICATIONS

Hidrate reusable water bottle, http://hidrate.me/, 6 pages.
Vessyl beverage tracking container, https://www.myvessyl.com, 3 pages.
Reiter, Wireless connectivity for the Internet of Things, Jun. 2014, Texas Instruments White Paper, 13 pages.

\* cited by examiner

HYDRATION SYSTEM AND METHOD THEREOF

CROSS REFERENCE TO RELATED APPLICATION

The present application is a continuation of U.S. patent application Ser. No. 15/691,144, filed on Aug. 30, 2017, which is a continuation application of U.S. patent application Ser. No. 14/657,300, filed on Mar. 13, 2015, now U.S. Pat. No. 9,792,409. Each of the above applications are incorporated herein by reference.

BACKGROUND

Technical Field

The present disclosure relates generally to the field of health tracking and monitoring devices. More particularly, the present disclosure relates to water bottles used in the health tracking industry. Specifically, the present disclosure relates to water bottles that transmit information of the amount of water or fluid consumed therefrom to a remote health tracking device and conveying that information to a user.

Background Information

Proper hydration is an integral aspect of human well-being. Water consumption is the primary way humans hydrate themselves. Often, people will carry around water bottles with them so they can hydrate on-the-go when they may not be near a water source.

Water bottles ordinarily include delineations thereon to indicate the amount of fluid contained in the bottle. Other water bottles may include digital representation of the amount of water contained in the bottle and consumed therefrom. One such exemplary digital water bottle is commercially available for sale under the name. of California. According to HydraCoach, their intelligent water bottle is an interactive fluid measurement device that automatically calculates, monitors and provides instant feedback on fluid consumption for athletes, amongst others. Determined by a user's weight and duration of exercise, the Hydracoach digital water bottle will generate a personal hydration goal for the day.

Shifting focus now to personal health tracking monitors (also known as "activity trackers"), they are exploding in popularity amongst individuals desiring to monitor many aspects of their daily health routine. Some exemplary personal health tracking monitors/devices are: Fitbit Surge and Fitbit Charge by Fitbit, Inc.; iWatch by Apple, Inc.; and Up and UP24 by Jawbone. Additionally, some smartphone applications operate as activity trackers, and some are even configured to sync with the aforementioned monitors/devices. Some exemplary smartphone applications are MyFitnessPal by MyFitnessPal, Inc. and RunKeeper by FitnessKeeper, Inc. Further, some of the heath tracking device companies have their own smartphone applications that collect and display information obtained from their device.

In these above referenced health monitoring mobile applications, there is often a line item entry for hydration (i.e., amount of water consumed). These mobile applications require the user to manually enter the amount of water they consume.

SUMMARY

Issues continue to exist with activity trackers and health monitoring mobile applications inasmuch as they require the manual entry of hydration information. A need continues to exist for a water bottle having the ability to calculate an amount of water consumed therefrom to directly sync with a remote device such as an activity tracker (e.g., Fitbit Surge, iWatch, or UP24, amongst many others) or a smartphone (e.g., iPhone) running a mobile health application. The present disclosure addresses these and other issues.

In one aspect, an embodiment may provide a communicative sports water bottle comprising: a bottle body having a base and an upwardly extending sidewall therein defining a fluid chamber; a sensor determining one or more of the following an amount of fluid in the fluid chamber, an amount of fluid being dispensed from the fluid chamber, and a physical movement of the bottle body; fluid information logic electronically coupled with the sensor creating digital data associated with fluid in the chamber; and data transmission and reception logic configured to send the digital data to a remote device and receive digital data from the remote device.

In another aspect, an embodiment may provide a method for displaying fluid consumption by a human comprising the steps of: displaying data associated with a first amount of fluid within a communicative bottle in a display; adjusting the amount of fluid in the communicative bottle by one of the following (a) dispensing fluid from the bottle and (b) adding fluid to the bottle; sensing the amount of adjusted fluid with a first sensor to create data associated with a second amount of fluid; and wirelessly sending data associated with the second amount of fluid to a remote device.

In another aspect, an embodiment may provide, in combination, a wearable health activity tracker including wireless communication logic and a water bottle including wireless communication logic, wherein the activity tracker and water bottle sync to one another to therebetween transfer data associated with fluid consumption by a user, the water bottle comprising: a bottle body having a base and an upwardly extending sidewall therein defining a fluid chamber. This embodiment may also include a software application executable on a mobile computing device displaying digital data associated with one of the following: an amount of fluid in the chamber, an amount of fluid dispensed from the chamber, an amount of time since fluid was last dispensed from the chamber, an amount of fluid dispensed over a given time period, a reminder notification if fluid has not been dispensed over a given time period, a reminder to consume an adjusted amount of fluid based, at least in part, on activity information obtained from the health tracking device. Additionally, this embodiment can include fluid consumption instructions for increased consumption by the user from the remote device to the bottle for display thereon when a second sensor, located on the remote device, detects one of the following an increase in physical activity by the user and an absence of drinking activity over a certain time period by the user.

In another aspect, the disclosure may provide a communicative water bottle that includes communication logic and wireless transmission logic technology electronically connected with a variety of sensors either on the water bottle or located remote from the water bottle. The sensors on the bottle create digital data associated with amount of fluid in the bottle and change thereof. The sensors remote from the bottle, which can be on an activity tracker, create digital data associated with an activity being performed by a user, such as running, or the absence of activity, such as remaining sedentary. A display on the bottle can indicate to the user the amount of fluid consumed or a reminder that fluid should be consumed. The fluid consumption data syncs with other remote devices such as mobile applications executable on smartphones.

BRIEF DESCRIPTION OF THE SEVERAL VIEWS OF THE DRAWINGS

A sample embodiment of the disclosure is set forth in the following description, is shown in the drawings and is particularly and distinctly pointed out and set forth in the appended claims. The accompanying drawings, which are incorporated in and constitute a part of the specification, illustrate various example methods, and other example embodiments of various aspects of the disclosure. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

Similar numbers refer to similar parts throughout the drawings.

DETAILED DESCRIPTION

Figure 1:
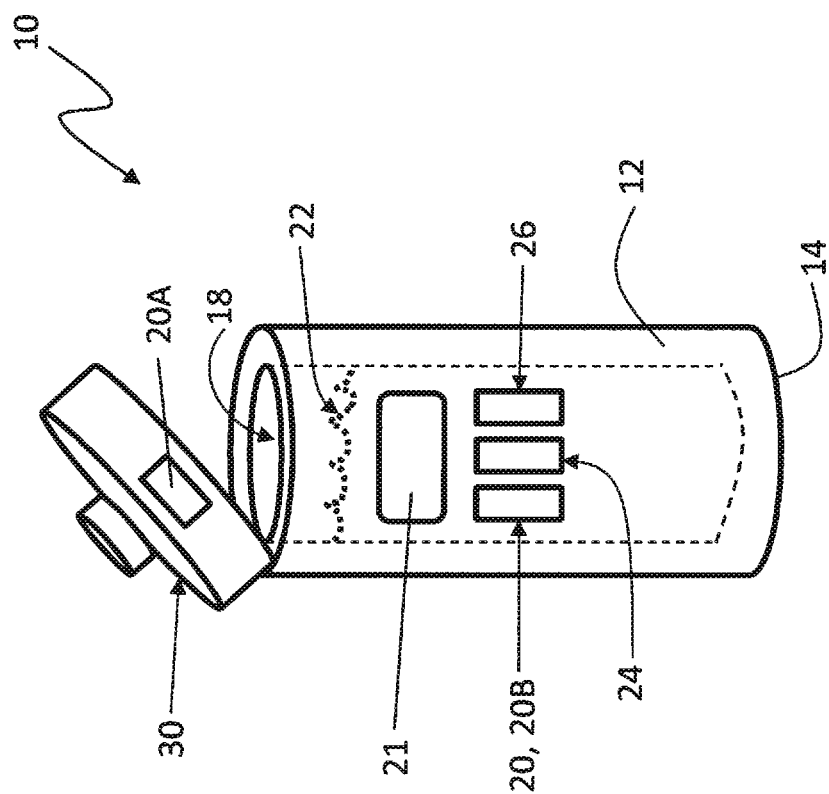
FIG. 1 is a diagrammatic representation of a communicative bottle of the present disclosure.

As depicted in FIG. 1, a communicative sports water bottle 10 of the present disclosure provides an improved way to communicate an amount of fluid (e.g., water) consumed by a person or otherwise dispensed over the course of a set time period. Further, bottle 10 provides an improved way to communicate the absence of fluid consumption (e.g., if a person is not drinking enough).

Sports water bottle 10 comprises a sports bottle body 12 having a base 14 and an upwardly extending generally rigid sidewall 16 therein defining a fluid chamber 18. Water bottle 10 further comprises a sensor 20 determining an amount of fluid 22 in the fluid chamber 18. Base 14 is a generally circular in shape when viewed from above and may include a slight apex at the center creating a generally dome formation, however it is not necessary. Sidewall 16 forms a rigid connection with base 14 extending upwardly therefrom. Sidewall 16 includes an outwardly facing outer surface and an inwardly facing inner surface. Inner surface of sidewall 16 defines a portion of chamber 18.

Bottle 10 further comprises fluid information logic 24 electronically coupled with the sensor 20 creating digital data associated with fluid 22 in the chamber 18. Bottle 10 may further comprise data transmission logic 26 configured to send the digital data to a remote device 28. The digital data may be displayed on a display 21.

"Logic", as used herein, includes but is not limited to hardware, firmware, software and/or combinations of each to perform a referenced function(s) or an action(s), and/or to cause a function or action from another logic, method, and/or system. For example, based on a desired application or needs, logic may include a software controlled microprocessor, discrete logic like a processor (e.g., microprocessor), an application specific integrated circuit (ASIC), a programmed logic device, a memory device containing instructions, an electric device having a memory, or the like. Logic may include one or more gates, combinations of gates, arrays, or other circuit components. Logic may also be fully embodied as software. Where multiple logics are described, it may be possible to incorporate the multiple logics into one physical logic. Similarly, where a single logic is described, it may be possible to distribute that single logic between multiple physical logics.

Water bottle 10 may further include a cap 30 repeatably attachable and detachable from the sports bottle body 12. In one embodiment, a sensor 20A may be located on or within the cap 30. Alternatively, a sensor 20B may be located on or integrally in the sports water bottle body 12. Sensors 20A and 20B may be similar to sensor 20 made reference to above and described in further detail below. Further, bottle 10 may include an indicator display 21 on the bottle body displaying the digital data associated with the fluid in the chamber. Indicator can also communicate to the user the time elapsed since the last consumption of fluid.

Cap 30 and body 12 may be formed substantially from a BPA-free material. Alternatively, cap 30 and body 12 may be constructed from another dishwasher safe material, such as stainless steel. Furthermore, the manner in which cap 30 is selectively released from engagement with body 12 can vary as one having ordinary skill in the art would understand. Cap 30 may threadedly attach and release from body 12 or may fit within the upper end of chamber 18 with a frictional interference fit including a sealing gasket. Further, cap 30 may include a nozzle permitting fluid 22 to flow therethrough.

The aforementioned electrical components of bottle 10 (i.e., the sensor 20, the display 21, the fluid information logic 24, and the transmission logic 26) may be powered by a rechargeable battery as one in the art easily understands. Furthermore, the battery and the electrical components powered therefrom may be constructed to be repeatably detached and attached to bottle 10 to allow for cleaning of bottle 10 without disturbing the electrical system which would may be damaged if contacted by water during washing and cleaning. While not shown, it is contemplated that the electrical components can be carried by a housing that nests within a recessed formed in body 12 facilitating the easy removal during cleaning.

Figure 2:
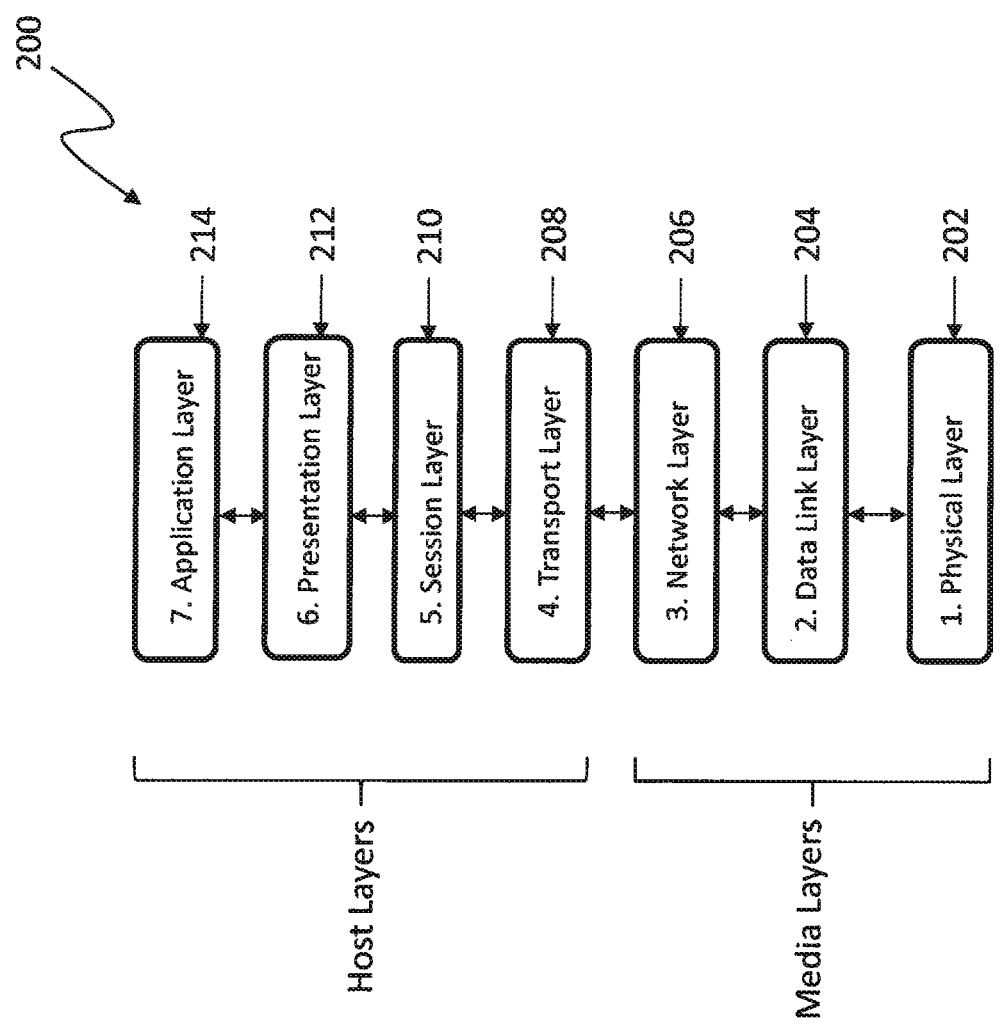
FIG. 2 is an exemplary display of a OSI seven layer model.

As depicted in FIG. 2, communicative sports bottle 10 may be used in combination with or include logic operable in one of, some of, or all seven layers of the Open Systems Interconnection model (OSI). The OSI model is a conceptual model that characterizes and standardizes the internal functions of a communication system by partitioning said system into abstraction layers. The model is a product of the Open Systems Interconnection project at the International Organization for Standardization (ISO), maintained by the identification ISO/IEC 7498-1.

The OSI modeling 200 includes a physical layer 202, a data link layer 204, a network layer 206, a transport layer 208, a session layer 210, a presentation layer 212, and an application layer 214. In one exemplary embodiment sports water bottle 10, the sensor 20A or 20B operates in one of the physical and data link layers 202, 204, respectively, or also the network layer 206. In another exemplary embodiment, the data transmission logic 26 operates in one of the physical 202, data link 204, network 206, transport 208, and session 210 layers. In another exemplary embodiment, the fluid information logic operates in one of the physical 202, data link 204, network 206, transport 208, session 210, presentation 212, and application 214 layers.

Figure 3:
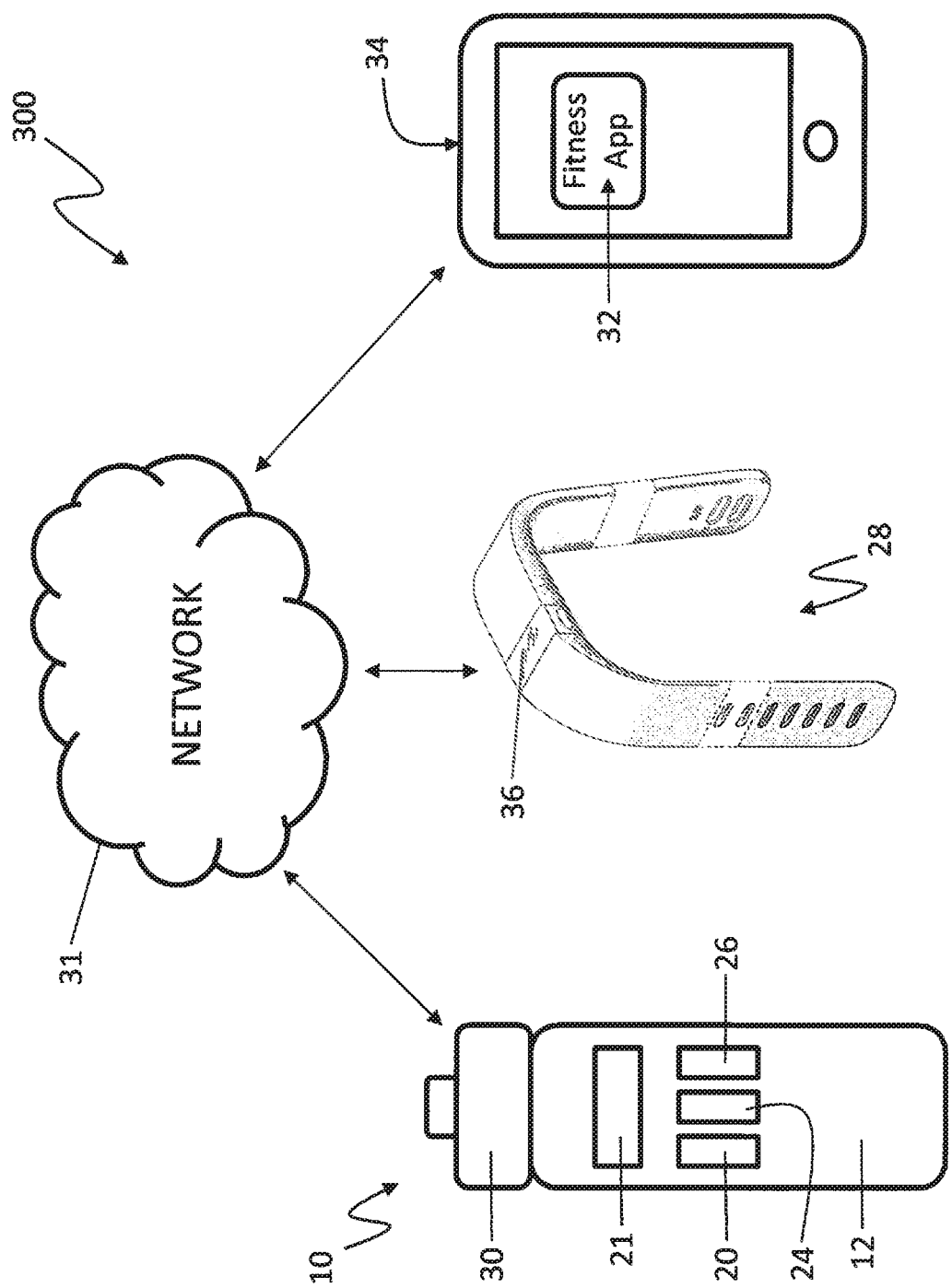
FIG. 3 is a diagrammatic representation of the communicative bottle of the present disclosure connecting to either one of a remote activity tracking device or a mobile application executable on a smart phone via a network.

As depicted in FIG. 3, the communicative sports water bottle 10 is used in combination 300 with one of a remote electronic health tracking device 28 (e.g., a Fitbit, an iWatch, or an UP24) and a mobile application 32 (e.g. MyFitnessPal) executable on a smartphone 34 (e.g., iPhone) and communication between devices occurs across network 31. The health tracking device 28 may further include a digital display 36. Both device 28 and mobile application 32 operate in one of the session, presentation, and application layers, 210, 212, and 214, respectively. Either one of device 28 and mobile app 32 display information associated with one or more of the following: an amount of fluid in the chamber, an amount of fluid dispensed from the chamber, an amount of time since fluid was last dispensed from the chamber, an amount of fluid dispensed over a given time period, and a reminder notification if fluid has not been dispensed over a given time period.

The fluid information logic 24 and data transmission logic 26 communicate with one of the remote devices (either device 28 or app 32 on smartphone 34) over network 31. The network 31 connectivity electronically couples the communicative sports water bottle 10 and the remote electronic health tracking device 28, wherein in the network connectivity is selected from a group comprising of: Bluetooth connection, wireless internet connection, wired internet connection, internet, and 3G/4G connection.

In operation, bottle 10 initiates data collection of water consumption through a plurality of triggers. One of the sensors 20 may include a detectable motion intensity signature. This motion intensity signature may be detected by the movement of bottle 10. An input to a trigger algorithm may come directly or indirectly from the sensor output. For example, the input may be direct output from an accelerometer or it may be processed accelerometer output. One exemplary trigger can be the lifting of the bottle 10 to activate the fluid information logic 24 which then initiates the sensor 20 to detect how much fluid or water is leaving the bottle 10.

Some movement of bottle 10 is considered activity associated with different levels of motion detected by a motion sensor of on bottle 10 carried by a user. In some conditions, a user grasps bottle 10 in a moving activity and drinks some of the fluid contained therein. In such conditions, the motion intensity detected by the motion sensor can initiate a data collection sequence by sensors coupled with fluid information logic or purposefully not initiate data collection. For example, repeated or rhythmic swaying of the bottle can be programmed (such as when clipped to a back pack or held in a hand while walking) to not initiate the data collection.

In operation, and during consumption, sensors 20 on bottle 10 may determine the rate of fluid exiting bottle 10 using a flow meter in cap 30. The flow-type sensors can measure fluid moving therethrough. Some exemplary manners of measuring fluid flow include determining by signal-to-noise ratio, signal norms, signal energy/power in certain frequency bands, wavelet scale parameters, and/or a number of samples exceeding one or more thresholds.

In other embodiments, accelerometer output power is used to determine different rates and amounts of fluid exiting bottle, where the rate of fluid leaving is calculated as a sum of accelerometer amplitude values (or amplitude squared values) relative to an exit orifice area. In some embodiments, data from one axis, or two axes, or three axes of one or more motion sensor may be used to determine the motion intensity. In some embodiments, data from one axis are used for further analyses when the signal is relatively high, while data from two or more axis are used for further analyses when the signal is relatively low.

In some embodiments, in addition to or instead of real time or near real time motion sensor data, previously processed and/or stored sensor information may be used to determine any one of the following an amount of fluid in the chamber, an amount of fluid dispensed from the chamber, an amount of time since fluid was last dispensed from the chamber, an amount of fluid dispensed over a given time period, and a reminder notification if fluid has not been dispensed over a given time period.

In some embodiments, information collected from sensors may include a record of information for a previous period (e.g., 1, 2, or 3 days to 6, 7 or 8 days) at a fixed time interval (e.g., once per minute; once per half hour; once per hour). Bottle 10 may further include artificial intelligence capable of learning such that digital information may be used to detect behavior signatures from the prior information, which may then be used to predict the likelihood of a subject has certain activity levels at the present time. Some embodiments use one or more classifiers or other algorithm to combine inputs from multiple sources (e.g., accelerometer power and minutely recorded data) and to determine the probability that the user is engaged in an activity with certain characteristics.

For instance, if a user tends to be drinking more frequently in the morning or during a meal but working and not drinking in the afternoon, the prior motion related data on the bottle will show data pattern reflecting the user's tendency, which tendency can be used by the bottle in a classifier connected to a computer or smartphone through the network to determine that the user is likely drinking water from bottle 10 with breakfast in the morning.

In operation, bottle 10 may include sensors located different positions along the bottle body or in the cap. With each sensor on bottle 10, placement-specific algorithms are run in order to estimate one of an amount of fluid in the chamber, an amount of fluid dispensed from the chamber, an amount of time since fluid was last dispensed from the chamber, an amount of fluid dispensed over a given time period, and a reminder notification if fluid has not been dispensed over a given time period. Adaptive filtering techniques may be used to cancel out excessive movements of the bottle (such as if bottle is being carried in a backpack).

A motion mode may be activated when the motion level is within a certain range. In the case of a sensor integrated into the cap, there may be three different motion level ranges corresponding to three modes; active mode, fluid movement mode, and inactive mode. The algorithmic determinations of and the transitions between the modes, which enable fluid measurement in a continuous manner. It should be noted that the three mode approach described herein is for illustration, and is not a limitation of the present disclosures. There may be fewer modes (e.g., active and not active) or greater than 3 modes.

In some embodiments, algorithms operating in the frequency domain are used to determine the number of times (i.e., the frequency) a person consumes fluid over a period of time. One problem people tend to have is that they do not drink enough water over the course of a day, especially people who exercise more frequently or those that need more water consumption (such as pregnant women). Frequency logic contained within the fluid information logic 24 counts the number of times a person is drinking per day or per hour and how much fluid is consumed within a given period. By way of non-limiting example, if a pregnant woman hypothetically needs to drink about 12 ounces of water every hour, frequency logic initiates and tracks the hourly time intervals ensuring that the required intake is met by the user.

In some implementations, bottle 10 may include one or more vibramotors (also referred to herein as "vibrators" or simply as "vibrating devices") for communicating information with or to the user. For example, the processing unit fluid information logic 24 or transmission logic 26 can utilize the vibramotors to communicate one or more alarms, achieved goals, progress indicators, inactivity indicators, reminders, indications that a timer has expired, or other indicators, feedback or notifications to a user holding or drinking from bottle 10. In some such implementations, the bottle 10 can utilize the vibramotors to communicate such information to the user in addition to communicating the same or similar information via the display, the lights, or the sound-producing devices. In some other such implementations, the bottle 10 can utilize the vibramotors to communicate such information to the user instead of or in lieu of communicating the same or similar information via the display, the lights, or the sound-producing devices. For example, in the case of an alarm when it is time to consume water (for example if the frequency logic determines that a pregnant woman has not consumed 12 ounces of water in the past hour), the vibramotors can cause the bottle 10 to vibrate to alert the user. As another example, in the case of a goal-achievement or progress indicator, the vibramotors can cause the bottle 10 to vibrate to alert the user that the user's goal has been achieved or that a milestone or other progress point en route to the goal has been reached without requiring the user to look at a display or hear an indication output from a speaker. In some implementations, a user can define one or more custom vibration patterns or other vibrational characteristics and assign such differing vibration patterns or other vibrational characteristics to different alarms, goals, or other vibrating indicators so that the user can distinguish among the vibrating indicators to determine what information is being communicated by the bottle 10. In various implementations, the user can customize such patterns, characteristics, or settings or make such selections via the user interface, or via an application or program (including a web application, mobile application, or client-side software program) executing on an external computing device (for example, a personal computer, smartphone or multimedia device) communicatively coupled with the portable monitoring device via the I/O interface and one or more wired or wireless connections or networks.

In some implementations, as described above, one or more of the sensors 20 themselves also can be used to implement at least a portion of the user interface. For example, one or more accelerometers or other motion sensors 20 can be used to detect when a person taps the body of bottle 10 with a finger or other object, and then interpret such data as a user input for the purposes of controlling the bottle 10. For example, double-tapping the body 12 of bottle 10 may be recognized by the fluid information logic 24 as a user input that will cause a display of the bottle 10 to turn on from an off state or that will cause the bottle 10 to transition between different monitoring states, sessions, or modes.

In accordance with one aspect of the present disclosure, bottle 10 has a shape and size that is adapted to be handled or carried by a user. Bottle 10 collects one or more types of fluid data from embedded sensors and/or external devices and communicates or relays such information to other devices or other internet-viewable sources. Notably, the bottle collects data regarding fluid consumed from bottle 10 over a time period, or the absence of consumption over that time period. In one example, the user carrying bottle 10 around with them during the course of a day. A display on the bottle can show the user how much fluid is inside the bottle, how much fluid has been consumed since the user woke up that day, or how much fluid has been consumed in the past hour. Additionally, bottle 10 can sync with a remote activity device 28 and determine how much fluid should be consumed based on the activity being performed. For example, if a user is wearing a Fitbit (remote device 28) and the Fitbit knows that a user is running, then water bottle 10 can adjust the consumption requirements for that activity. Furthermore, bottle 10 can even further adjust the consumption requirements of fluid based on the activity and the user's biometrics (i.e., weight, gender, age). The consumption data or alerts may then be transmitted and displayed to the user.

In accordance with another aspect of the present disclosure, bottle 10 may communicate to a user how much fluid needs to be consumed based on an activity level being performed during or over a given time period. For example, bottle 10 communicates with a remote activity device 28, such as a Fitbit. Fitbit device 28 learns and understands increases in activity by the person as the device 28 is carried or worn by a user. So for example, a predominately stationary or sedentary person may only need to consume about 64 ounces of water a day. The device 28 communicates the person's sedentary nature to bottle 10 and a first amount of water (64 ounces) is displayed to the user setting a consumption goal for the day. However, when the sedentary person decides to start exercising, the Fitbit device 28 will register and sense increased physical activity. The physical activity requires more water consumption by the user of the water bottle. The water bottle will adjust the amount of water to be consumed based, at least in part, on the activity and physical exertion performed by the person. So if the person begins running for a 30 minutes, the bottle will adjust the required fluid consumption and display a second amount, for example an additional 32 ounces for a total daily consumption of 96 ounces. Clearly, the actual amounts of the first and second consumption amounts are based on individual biometrics such as age, gender, and weight.

In operation, the data transmission logic 26 communicates consumption data received from the fluid information logic 24 coupled with sensors 20 via the I/O interface to an external or remote computing device 28 or smartphone 34 (for example, a personal computer, smartphone or multimedia device) or to a back-end server over one or more computer networks. In some implementations, the I/O interface included in transmission logic 26 includes a transmitter and a receiver (also referred to collectively herein as a "transceiver" or simply as "transmitting and receiving circuitry") that can transmit the activity data or other information through a wired or wireless connection to one or more external computing devices or to one or more back-end servers (either directly via one or more networks or indirectly via an external computing device that first receives the activity data and subsequently communicates the data via one or more networks to the back-end servers). In some implementations, the one or more computer networks include one or more local-area networks (LANs), private networks, social networks, or wide-area networks (WANs) including the Internet. The transmission logic 26 includes wireless communication functionality so that when the bottle 10 comes within range of a wireless base station or access point, or within range of certain equipped external computing devices (for example, a personal computer, smartphone 34 or remote activity device 28), certain activity data or other data is automatically synced or uploaded to the external computing device or back-end server for further analysis, processing, viewing, or storing. In various implementations, the wireless communication functionality of I/O interface may be provided or enabled via one or more communications technologies known in the art such as, for example, Wi-Fi, Bluetooth, RFID, Near-Field Communications (NFC), Zigbee, Ant, optical data transmission, among others. Additionally or alternatively, the I/O interface also can include wired-communication capability, such as, for example, a Universal Serial Bus (USB) interface.

Some exemplary sensors 20 capable of being electronically coupled with bottle 10 (either integrally on bottle 10 or remotely connected thereto) may include but are not limited to: accelerometers sensing accelerations experienced during rotation, translation, velocity/speed, location traveled, elevation gained; gyroscopes sensing movements during angular orientation and/or rotation, and rotation; altimeters sensing barometric pressure, altitude change, flights of stairs, climbed, local pressure changes, submersion in liquid; impellers measuring the amount of fluid passing thereby; Pulse Oximeter sensing blood oxygen saturation (SpO2), Heart rate variability, stress levels, heart rate, blood volume active heart rate, resting heart rate, sleeping heart rate, sedentary heart rate, cardiac arrhythmia, cardiac arrest, pulse transit time, heart rate recovery time, and blood volume; Galvanic Skin sensors sensing electrical conductance of skin, perspiration, stress levels; Response Sensors sensing exertion/arousal levels; Global Positioning sensors sensing location, elevation, distance traveled, velocity/speed; Electromyography sensors sensing electrical pulses; Muscle tension/extension sensors; Audio Sensors sensing local environmental sound levels, laugh detection, breathing detection, snoring detection, respiration type (snoring, breathing, labored breathing, gasping), voice detection, typing detection; Photo/Light sensors sensing ambient light intensity, ambient Day/night, sleep, UV exposure; TV sensors sensing light wavelength watching, indoor v. outdoor environment; Temperature sensors sensing body temperature, ambient air temperature, and environmental temperature; Respiration rate sensors sensing respiration rate; Sleep apnea detection sensors; Blood Pressure sensors, and Moisture Sensors sensing surrounding moisture levels.

In the case where the data is relayed from a remote/external sensor on remote device 28 to bottle 10, or from a sensor on bottle 10 to either a remote device 28 or smartphone 34, the digital data may indicate to the bottle 10 that the data should be relayed. For example, the data transmission may contain a code that tells the bottle 10 to relay the data. In another example, the relay indicator may not be an addenda to the message, but rather something inherent to the data itself. For example, if the data has a certain type of encryption, the encryption type may indicate that the bottle 10 should forward the data to a computing device. Note that being unencrypted may be considered an encryption type. Syncing may occur through wired and/or wireless connections including but not limited to USB, Wi-Fi, WiMAX, Mobile telephony (i.e. cellular networks), Bluetooth, Bluetooth Smart, NFC, RFID, and ANT.

Additionally, bottle 10 may incorporate one or more user interface and/or feedback methods such as visual methods, auditory methods, or haptic methods (such as touch input or vibration). The device may display the state of one or more of the information types available and/or being tracked. For example, information can be displayed graphically, or conveyed by the intensity and/or color of one or more light emitting diodes (LEDs). The user interface may also be used to display data from other devices or internet sources. The device may also provide haptic feedback to the user through, for instance, the vibration of a motor or a change in texture or shape of the device.

In one embodiment, the bottle 10 may not have a display. The device may instead communicate information to the user using one of the other user feedback methods described herein (e.g. one or more LED's, haptic feedback, audio feedback). In another embodiment, the device may not communicate information to the user directly. Instead, the user may view their information on one or more remote computing devices (i.e., smartphone 34) in direct or indirect communication with the bottle 10. In the case that the communication is indirect, data may be transferred from the device to one or more intermediate communication devices (e.g. networks server or nodes) which then forwards the information to the secondary computing device (remote device 28 or smartphone 34) used to view data. For example, data may be transferred from the device through a smartphone to a server that hosts a website containing the user's data.

One example of communications between a portable biometric device, handheld bottle 10 and computing device is illustrated in FIG. 3. Initially the bottle 10 may send a notification signal to notify any nearby handheld activity device 28 or smartphone 34 of its presence. Once an activity device 28 or smartphone 34 receives one of these alerts, bottle 10 may sync data with the activity device 28 or smartphone 34. Fluid consumption related data which is sent from bottle 10 without an indication that the data should be relayed is displayed and/or stored on a first database on the remote device 28. Data with a relay indication is forwarded onto a computing device where the data is stored in a second database. Relayed data may also be displayed and stored on the bottle 10.

In one particular embodiment, data transmission logic 26 may broadcast a notification signal to remote device 28. The bottle 10 may indicate, in the notification signal or a characteristic of the notification signal, whether the bottle 10 device seeks (or requests) to sync or establish a communication link with the remote device 28 through network 31. In the case that the bottle 10 does not seek to establish a communication link with the remote device 28, the bottle 10 may still take action to establish a communication link and sync or not.

Consumption data created from sensors 20 coupled to fluid information logic 24 on bottle 10 may be used by a mobile application, such as MyFitnessPal executed on the portable communication device (e.g. smart phone 34). Users of bottle 10 may have accounts on such applications or services which allow them to retrieve data relevant to themselves or other users. An account may enable a user to visualize their fluid consumption data, modify data visualizations, modify or enter additional or existing data, manage their devices, and/or interact with other users. Fluid consumption data synced from the bottle 10 may be used for account features including but not limited to a leader board where the user is ranked compared to other users such as friends, rankings of members of a group of users, and badge awards to reaching various goals, such as meeting or exceeding your consumed fluids for a day. The user account may also automatically provide recommendations to the user so as to help them reach one or more goals including but not limited to increasing or decreasing their water consumption, weight, body fat, time asleep, quality of sleep, calorie burn, activity level, resting heart rate, active heart rate, normal heart rate, steps taken, distance walked and/or run, and floors climbed, all of which can be displayed on the water bottle display.

These recommendations may aid the user in short term and/or long term goals. For example, if a user has not been consuming the proper amount of water over the few days or even the last month and has started to have headaches and other side effects from improper hydration, bottle 10 may be recommend to be more water consumption through a notification on directly to the display on bottle 10, or to the wearable remote device 28, or an health application 32 executable on smartphone 34. On a shorter time scale, a user may be recommended to drink a certain amount of water with dinner if they were did not drink much water earlier in the day. In order for such short term recommendations to be relevant to the user's current state, data synced from their device which help determine the recommendation is preferably transferred frequently and/or whenever there is new data on the device relevant to such a recommendation.

In one embodiment, the bottle 10 and the remote device 28 communicate using the Bluetooth Smart protocol. The bottle 10 may intermittently broadcast one of two UUID's (universally unique identifiers) to the remote device 28 or smartphone 34 which is constantly listening for broadcasts. The first UUID corresponds to a Bluetooth service which is used to sync new data from the sensor device. This service is configured to start any programs on the smartphone 34 necessary to sync the new data from the sensor device. The second UUID corresponds to a Bluetooth service which is only used when a program on the bottle 10 needs to send data to the remote device 28 or smartphone 34.

Bottle 10 may monitor its wireless input sources for incoming wireless packets and analyze any received packets in order to detect the smartphone 34 or activity tracker device 28 as the source of their transmission and decide whether to sync with the remote device. The function or functions within the bottle 10 that monitors input sources for and analyzes packets may be embedded within the operating system of the bottle 10 and/or in an application or applications that are launched by the operating system of the bottle 10 (i.e., the input monitoring and/or packet analysis functions may be implemented by execution, within one or more processors of the communications device, of programmed instructions that form part of the bottle 10 operating system and/or application programs). The packet detection functionality may be automatically launched or executed by the operating system or can be initiated or directed by the user or users of the bottle 10. If the functionality is partially or fully within an application, application or applications may be launched automatically by the operating system or launched by the user or users of the bottle 10. The packet detection functionality may also be split between the operating system and applications. The functionality can execute or run in any priority or mode (active, foreground, background, etc.) on any processor within the bottle 10. The functionality can also run simultaneously with other functions on the same bottle 10. If the functionality has already been launched (i.e., implemented through execution of programmed instructions), the operating system can choose to execute or re-execute the functionality, which might be resident in volatile or non-volatile storage or memory of the bottle 10.

Listening (monitoring input sources) for incoming packets may be carried out periodically in order to lower power consumption (e.g., by powering down or otherwise disabling signal reception functions during intervals in which input sources are un-monitored), or continuously in order to decrease the time to detection ("detection latency"). Also, the frequency of periodic listening events may be varied to balance power consumption and the time to detection. During a previous interaction, a user or computer, either directly via input on the display 21 of bottle 10 or via a wired or wireless communication mechanism, may specify which aspects of the contents of a wireless packet or sequence of wireless packets should trigger a data sync by the bottle 10. Any single piece of information or combination of the information in a wireless packet or sequence of packets may trigger a data sync after receipt and analysis of the packets. When the sync is triggered, the bottle 10 may start and complete the syncing process via functionality that is embedded within the operating system of the bottle 10 or via an application that is launched by the operating system of the bottle 10. The initiation, start, and/or completion of a sync may be performed with or without user interaction using techniques described herein.

The bottle 10 may determine whether or not it needs to sync based on fluid consumption goals of the user. The user may set these goals themselves or they may be set automatically based on weight, gender, age, typical activity level of a person wearing the activity tracker 28. The bottle could use the type of goal to determine when it should sync. For example, if the user has a goal based on the ounces they desire to drink in a given day, the bottle may sync only when it detects that the user consumed that amount of water. The criteria for meeting a goal may also be used by the device to determine when it should sync. For example, if a user's goal is to drink 64 ounces of water, the device may try to sync when the user has reached 50%, 75%, and 100% of their goal. This would ensure that the user can see a reasonably precise measure of the progress to their goal on computing devices, portable communication devices, and/or web-based accounts associated with their device.

Bottle 10 may also sync based on when a user interacts with a remote activity tracker device 28 which displays synced data or data derived from synced data. In one embodiment, a network server, bottle 10, sensor 20 or some combination of the three may determine, based on historical data when the user views synced data or information derived from synced data on their activity device 28 or smartphone 34. In one example, the bottle 10 may sync to the user's activity device 28 or smartphone 34 every time the user wakes up their activity device 28 or smartphone 34 from sleep mode or turns on their activity device 28 or smartphone 34. This would allow the user to see the most up to date information when checking their data on the activity device 28 or smartphone 34. In another example, if a user always checks their smart phone at lunch time to see how much water they have drank that morning, the bottle 10 may learn this habit and sync data immediately before the user's lunch time so that the most up to date water consumption is displayed.

The bottle 10 may determine whether or not it needs to sync based on the activity of the user. In one embodiment, for example, the bottle 10 includes a motion sensor 20 configured (e.g., through a programmable setting) to sync when the motion sensor detects that the user is active and drinking from the bottle.

In a plurality of embodiments, bottle 10 is capable of changing the device identifier and/or owner identifier based on the device's intent to sync, a particularly useful feature in cases where a mobile communication device listens for and initiates sync operations solely based on device or service unique identifiers. Typically, such a mobile communication device might initiate a sync whenever the sensor device came within range or stayed within range, thus potentially syncing more frequently than desirable and consuming undue power. By enabling the sensor device to dynamically change its device, service or owner identifier, however, and to set such identifier(s) to values recognized by the mobile communication device only when new data is available to sync, the mobile communication device would only initiate a sync when necessary, since the mobile communication device would only listen for identifiers that indicated that the sensor device needed to sync. This operation also enables the sensor device sync to co-exist and sync optimally with other communications devices that could base their decisions to sync on using more information contained in a sensor device's wireless packets.

The remote device 28 or smartphone 34 may communicate with bottle 10 via network servers located on private networks or public networks such as the Internet. Through an interface located on a server or a communications device that may communicate with that server, a user may change settings, data or behavior on or of a sensor device, for example by providing instructions to program or otherwise load configuration data or settings into one or more configuration registers of the sensor device. These changes may include but are not limited to parameters for algorithms, time and alarm settings, personal biometric information (weight, height, age, gender, base metabolic rate, etc.), settings for the user interface (which UI screens to show, what information to show on each screen, the order of screens, etc.). Once a change is made, this change may be synced to a sensor device.

The term "sync" refers to the action of sending and/or receiving data to and/or from bottle 10 to a computing device 34 and/or remote activity tracking device 28 as seen in FIG. 3. "Sync" may also be used in reference to sending and/or receiving data to and/or from another computing device or electronic storage devices including but not limited to a personal computer, cloud based server, and database. In some embodiments, a sync from one electronic device to another may occur through the use of one or more intermediary electronic devices acting as a portal. For example, data from a bottle 10 may be transmitted to a smart phone that relays the data to a server. The data may then be viewed on other network/server-connected devices as shown in FIG. 3.

Some exemplary methods for use of bottle 10 may include a method for displaying fluid consumption by a human comprising the steps of: displaying data associated with a first amount of fluid within a communicative bottle in a display; adjusting the amount of fluid in the communicative bottle by one of the following (a) dispensing fluid from the bottle and (b) adding fluid to the bottle; sensing the amount of adjusted fluid with a first sensor to create data associated with a second amount of fluid; and sending data associated with the second amount of fluid to a remote device. This method may further include the steps of receiving activity information of a person at the bottle from a second sensor on the remote device; and adjusting the data associated with the first amount of fluid, based at least in part, on the activity information received from the sensor, and displaying data associated with a third amount of fluid in the display. Alternatively, this exemplary method may include wherein the sensor is on a remote device and the activity information is associated with physical movement of a person carrying the remote device. Alternatively, this exemplary method may include wherein the first sensor is integral to the communicative water bottle. Further, this exemplary method may include the additional steps of displaying data associated with a third amount of fluid to be consumed by a person contained in the bottle in the display; receiving activity information of the person from a remote activity device; and adjusting the third amount of fluid to be consumed by the person based, at least in part, on the activity information received from the remote activity device, and displaying a second amount of fluid to be consumed in the display. Alternatively, this exemplary method may include wherein the first sensor is a flow sensor and the activity information is drinking the fluid by the person, and further comprise the steps of: sensing the difference between the second amount of fluid and the first amount of fluid after the person has drank the fluid creating consumption data; transmitting the consumption data from the communicative bottle to the remote device selected from a group comprising a remote activity tracker and a mobile application executable on a smartphone. And, this exemplary method may include the steps of syncing the water bottle with the remote device based, at least in part, on the activity information obtained from the sensor, wherein the sensor is on the bottle.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the preferred embodiment of the disclosure are an example and the disclosure is not limited to the exact details shown or described.

What is claimed:

1. A hydration system comprising:
   a bottle body having a base and an upwardly extending sidewall therein defining a fluid chamber and a first display coupled to the bottle body;
   a sensor determining one or more of the following an amount of fluid in the fluid chamber, an amount of fluid being dispensed from the fluid chamber, and a physical movement of the bottle body;
   fluid information logic electronically coupled with the sensor creating digital data associated with fluid in the chamber;
   data transmission and reception logic configured to send the digital data to a remote device and receive digital data from the remote device, wherein the data transmission and reception logic monitors wireless input sources for incoming wireless packets and analyzes any received packets in order to detect a source of the packet transmission and decide whether to sync the digital data associated with fluid in the chamber with the source of the packet;
   wherein the remote device is an electronic device executing a health activity tracker, the remote device including a second display that displays information associated with one or more of the following: the amount of fluid in the chamber, the amount of fluid dispensed from the chamber, an amount of time since fluid was last dispensed from the chamber, an amount of fluid dispensed over a given time period, a reminder notification if fluid has not been dispensed over a given time period, a reminder to consume an adjusted amount of fluid based, at least in part, on activity information obtained from the remote device;
   network connectivity electronically connecting the data transmission and reception logic and the remote device, wherein in the network connectivity is selected from a group comprising of: Bluetooth connection, wireless internet connection, wired internet connection, internet, and 3G/4G connection;

a record of information for a previous period at a fixed time interval, and the record of information is displayed in one of the first display and the second display;

a cap repeatably attachable and detachable from the bottle body, and wherein the sensor is carried by the cap; and cap sensor placement-specific algorithms executed by the fluid information logic during the previous period to determine the one or more of the following the amount of fluid in the fluid chamber, the amount of fluid dispensed from the fluid chamber, the physical movement of the bottle body, the amount of time since fluid was last dispensed from the chamber, the amount of fluid dispensed over a given time period, and the reminder notification if fluid has not been dispensed over a given time period; and adaptive filtering logic executed during the previous period to cancel out excessive movements of the cap.

2. The hydration system of claim 1, further comprising:

artificial intelligence configured to learn the record of information to detect behavior signatures from the previous period, which is implemented to predict a likelihood of a subject has certain activity levels at a present time.

* * * * *